United States Patent [19]

Parins

[11] Patent Number: 5,192,280
[45] Date of Patent: Mar. 9, 1993

[54] PIVOTING MULTIPLE LOOP BIPOLAR CUTTING DEVICE

[75] Inventor: David J. Parins, Columbia Heights, Minn.

[73] Assignee: Everest Medical Corporation, Minneapolis, Minn.

[21] Appl. No.: 797,531

[22] Filed: Nov. 25, 1991

[51] Int. Cl.$^5$ .............................................. A61B 17/39
[52] U.S. Cl. ........................................ 606/48; 606/50
[58] Field of Search ...................... 606/46, 50, 45, 48, 606/49; 128/7

[56] References Cited

U.S. PATENT DOCUMENTS

| | | | |
|---|---|---|---|
| 749,689 | 1/1904 | Houghton | 606/171 |
| 1,620,828 | 3/1927 | Molony | 606/49 |
| 1,770,653 | 7/1930 | Molony | 606/49 |
| 1,967,015 | 7/1934 | Wappler | 606/49 |
| 2,002,559 | 5/1935 | Wappler | 606/46 |
| 2,002,594 | 5/1935 | Wappler et al. | 606/46 |
| 2,004,559 | 6/1935 | Wappler et al. | 606/46 |
| 2,028,635 | 1/1936 | Wappler | 606/46 |
| 3,144,020 | 8/1964 | Zingale | 128/4 |
| 3,901,242 | 8/1975 | Storz | 606/46 |

*Primary Examiner*—Lee S. Cohen
*Assistant Examiner*—Marianne Harley
*Attorney, Agent, or Firm*—Haugen and Nikolai

[57] ABSTRACT

An electrosurgical cutting instrument with bipolar electrodes integrally formed into a pivoting ceramic working head. The ceramic head is pivotable about a pivot point by selectively retracting a substantially rigid wire internal to a working element which is slidably and rotatably received within an introducer and connected to a point on the ceramic head offset from a longitudinal axis. Radial incisions are induced into a prostate gland during a transurethral resectioning of the prostate gland (TURP) by applying an RF energy across the bipolar electrodes from an external power source and drawing the electrodes across prostate gland tissue. The pivotal head can be selectively reciprocated to approximately a 90° angle relative to a longitudinal axis of the introducer to effectively cauterize tissue during surgery to perform resectioning of the prostate. Increased maneuverability of the instrument allows a surgeon to more quickly and effectively complete a TURP. The electrodes may be formed in various shapes out of ductile tungsten alloy to withstand high operating temperatures depending upon the nature of the cutting desired. The cutting instrument is suitable for other surgical procedures as well performed using an endoscope.

13 Claims, 3 Drawing Sheets

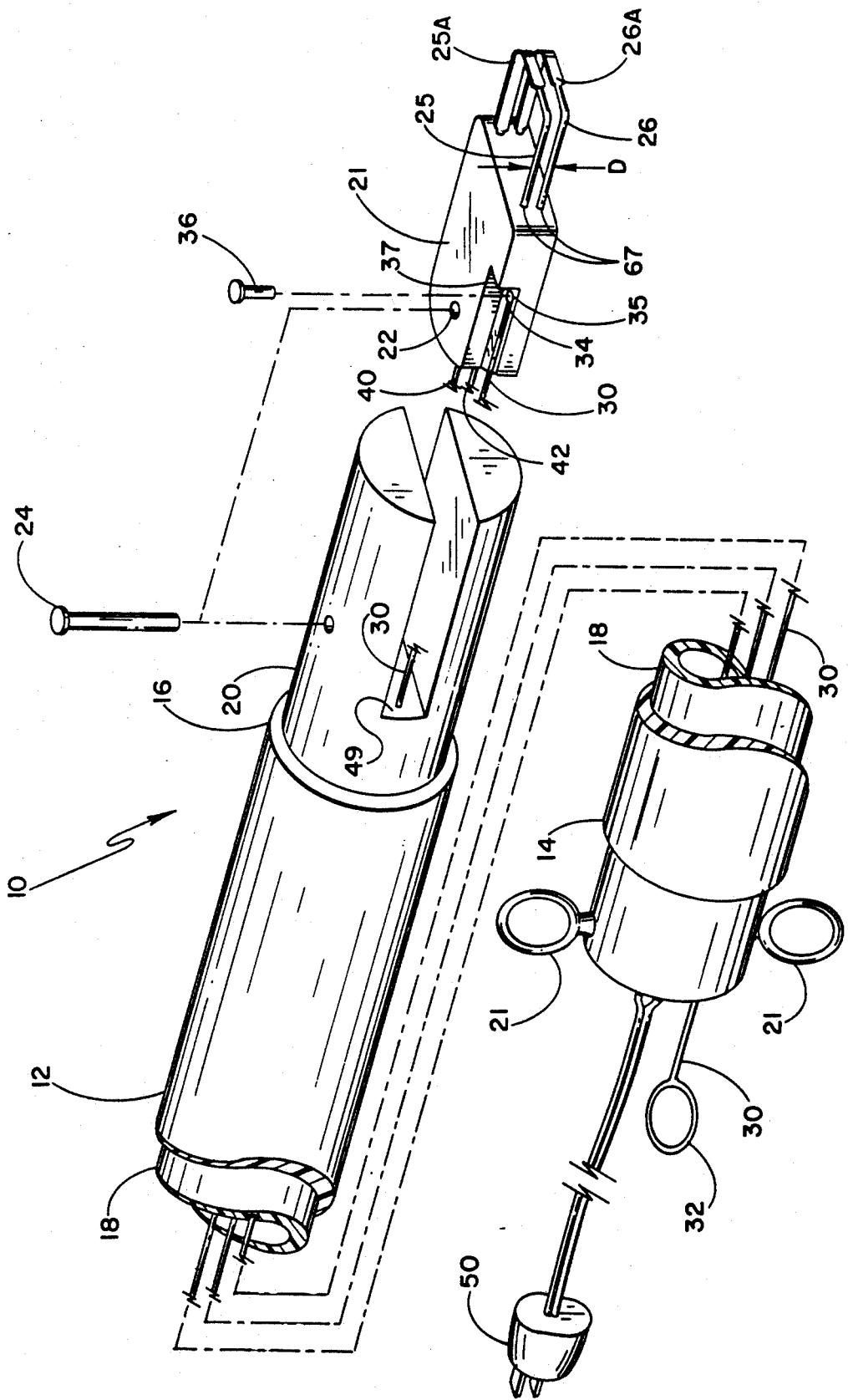

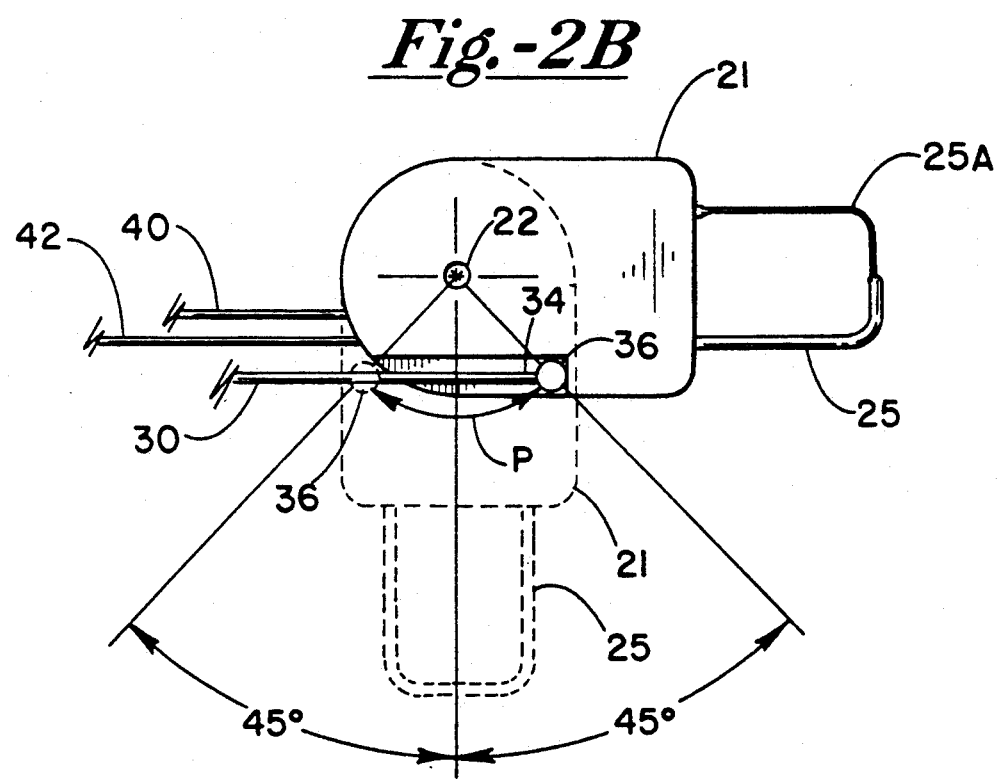

PIVOTING MULTIPLE LOOP BIPOLAR CUTTING DEVICE

BACKGROUND OF THE INVENTION

1. Field of the Invention

This invention relates generally to the design of an electrosurgical device and, more particularly, to a bipolar device having specially designed electrodes which are maneuverable for facilitating cutting to create a cut plane perpendicular to the device shaft.

2. Discussion of the Prior Art

To perform a transurethral resectioning of the prostate (TURP), an electrosurgical instrument is typically used to create radial slices in the prostate gland. These cutting devices are inserted through the urethral passage to the site and then electrodes are energized by an external power source to cut and cauterize tissue proximate the electrodes.

U.S. Pat. No. 3,144,020, issued to Zingale, teaches a removable doturator tip for guiding a sheath into a urethral passage, where a cauterizing tip is inserted into the sheath after the sheath is in place. This instrument suffers from substantially no maneuverability of the inserted cauterizing tip during surgery and is time consuming. Further, the instrument comprises two separate pieces.

Further prior art devices taught in U.S. Pat. Nos. 2,004,559 and 2,002,594 to Wappler, et al., teach electrosurgical instruments with jaws. Only one electrode is attached to the jaws having limited arcuate maneuverability and is partially obstructed by the jaws. Another device taught in U.S. Pat. No. 2,002,559, also to Wappler, et al., teaches an instrument with one sliding electrode which rocks side to side rather than pivoting.

U.S. Pat. Nos. 1,620,828 and 1,770,653 to Molony teach a single monopolar electrode instrument having an insulating, beak-like tip rotated by two metal rods. An alternative surgical approach is to effect longitudinal cuts in the prostrate rather than bulk tissue removal.

It is accordingly a principal object of the present invention to provide an improved bipolar electrosurgical cutting instrument.

Another object of the present invention is to provide a bipolar electrosurgical cutting instrument having a maneuverable working head. When in its axial position, it should present a low profile.

A further object of the present invention is to provide a bipolar electrosurgical cutting instrument having a maneuverable head which can reciprocate to create radial slices in the prostate gland. The instrument should be insertable into the urethral passage for locating a working head proximate the prostate gland and capable of being electrically energized by an external power supply.

It is another object of the invention to provide an electrosurgical instrument having a maneuverable head which can maneuver approximately 90° to enhance the cut and coagulation function of an endoscopic and laparoscopic device.

SUMMARY OF THE INVENTION

The foregoing objects and advantages of the invention are achieved by providing an electrosurgical cutting instrument with a pivoting working head which includes a pair of closely-spaced bipolar electrodes. In the preferred embodiment, a generally tubular introducer includes a proximal end and a distal end. A generally tubular working element having a proximal end, a distal end and a lumen therebetween is received within the introducer wherein the distal end extends beyond the distal end of the introducer. A head member comprised of an insulating material is pivotally mounted at a pivot point on the distal end of the working element. A pair of closely spaced bipolar electrodes extend outward from the head member in the longitudinal direction and are physically separated from one another. A pair of conducting wires insulated from one another each extend through the lumen and connect at one end individually to the pair of bipolar electrodes, wherein the other end of the conducting wires facilitate connection to an external power source. Wire means extends through the lumen and connects to the head member for pivoting the head member about the pivot point. The wire means is sufficiently rigid such that motioning the wire means towards and away from the proximal end of the introducer creates rotation of the head member about the pivot point.

The insulating material of the pivoting head member is preferably formed of a suitable ceramic or plastic material having a high melting point and integrally formed about leg portions of the bipolar electrodes. The bipolar loop-shaped electrodes are rigidly supported in a close side-by-side relationship and can readily be fabricated from ductile wire, for example, tungsten or tungsten alloy. This can be done by appropriate wrapping of wire about a forming mandrel, and because the tungsten alloy wire can be of an appropriate gauge to insure rigidity, the electrode segment is very inexpensive to manufacture and holds up well over prolonged periods of use in electrosurgical procedures. An electrical connection is made within the lumen of the tubular introducer between the leg portions of the bipolar electrodes and a plug member which is connectable to an external electrosurgical power source.

The wire means is preferably comprised of a wire formed of a sufficiently rigid material such as stainless steel. The wire means is preferably attached to the pivoting head member at a point which is offset from a longitudinal axis of the introducer when the bipolar electrodes are generally aligned in a coaxial fashion to facilitate rotation. The introducer is preferably comprised of a medical grade plastic.

Still further embodiments feature a pair of closely-spaced parallel bipolar hook-shaped electrodes. The wire conductors forming the electrodes can be stretched into other various shapes, including a pair of elongated loops, a pair of triangular-shaped loops, a pair of J-shaped loops or a pair of L-shaped loops, positioned at various angles relative to the pivotable ceramic head member. A larger surface area can be added to add the coagulation function to the electrode elements.

The electrosurgical instrument is adaptable to other surgical procedures as well which implement an endoscope where a pivoting bipolar cutting head is desirable.

BRIEF DESCRIPTION OF THE DRAWINGS

Other objects, features and advantages of the present invention will become apparent to those skilled in the art through the Description of the Preferred Embodiment, Claims, and drawings herein wherein like numerals refer to like elements.

FIG. 1 is a perspective view of the electrosurgical cutting instrument having a pivotable head with bipolar electrodes in accordance with the preferred embodiment of the present invention;

FIG. 2B is a sectional view of the pivoting head illustrating the 90° pivoting feature of the pivoting head.

DESCRIPTION OF THE PREFERRED EMBODIMENT

Figure 2A:
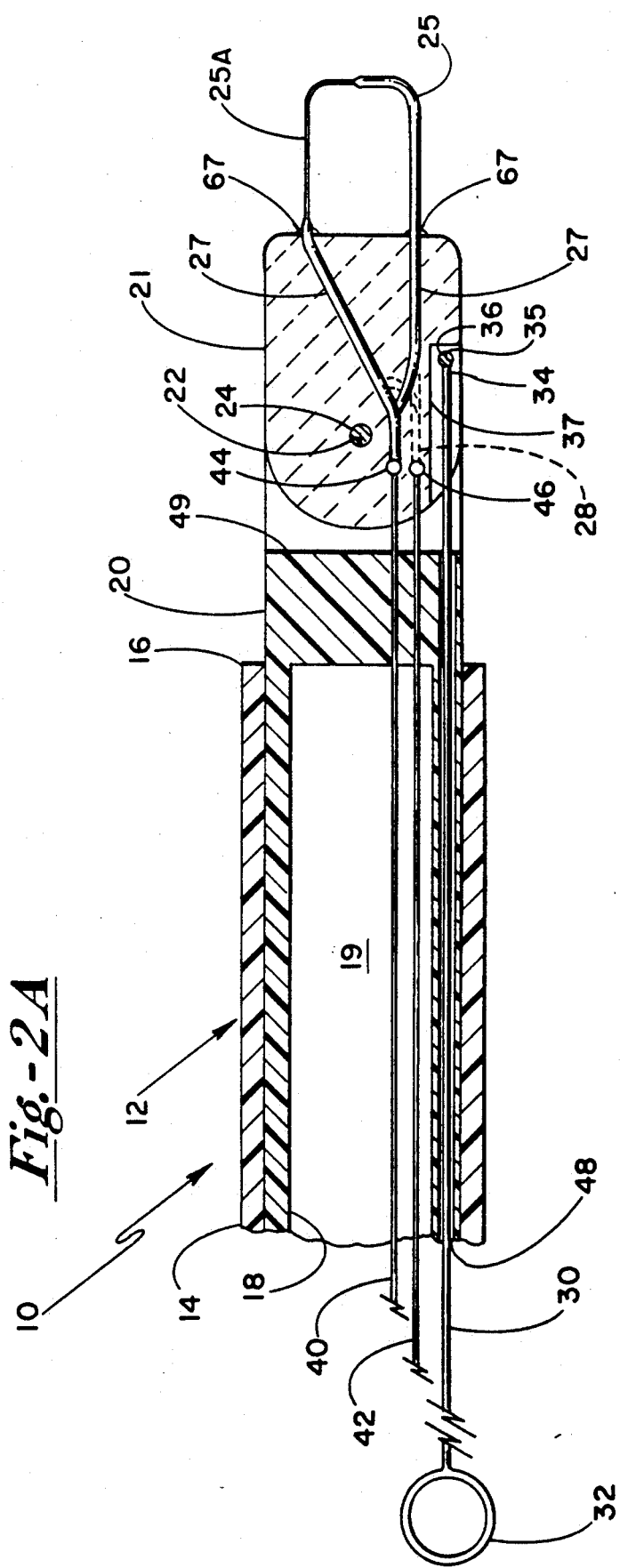
FIG. 2A is a sectional view of the electrosurgical cutting instrument illustrating the integral arrangement of key elements including a pivoting wire, a pivoting head, cut electrodes, and a coagulation electrode portion.

Referring to FIG. 1, there is indicated generally by numeral 10 an electrosurgical cutting instrument constructed in accordance with the preferred embodiment of the present invention. The instrument comprises an elongated tubular introducer 12, preferably extruded from a suitable medical grade plastic, having a proximal end 14 and a distal end 16. A generally tubular working element 18, also comprised of medical grade plastic, is slidingly and rotatably received within introducer 12. Working element 18 has a pair of loop holes 21 at a proximal end, and a lumen 19 extending from the proximal end to a yoke-like distal end 20 located exterior of introducer 12. The yoke 20 has a rectangular notch formed inward from its distal end. Generally plate-like head member 21 is received in the notch defining wall 49 of yoke 20 and preferably is fabricated from an insulating ceramic or a high melting point plastic material. Head member 21 is pivotally attached at a centrally located pivot hole 22, by pivot pin 24, such as a rivet.

Closely aligned bipolar electrodes 25 and 26 are inserted into apertures formed in the distal end of ceramic head member 21 and extend outward therefrom. Electrodes 25 and 26 are preferably formed from a suitable ductile wire, preferably tungsten alloy, and are separated by a relatively small distance "D". The wire diameter may be approximately 0.010 inch to 0.030 inch, but limitation to the tungsten material and that dimension is not to be inferred. Each electrode 25 and 26 has a flattened portion 25A and 26A for coagulation formed by compressing a tubular element. Flattened portions 25A and 26A each extend approximately half the length of each electrode and provide a larger surface area for coagulating rather than cutting the proximate tissue.

A pull-wire 30 is longitudinally disposed in working element 18 and extends from a loop-shaped handle portion 32 at its proximal end, disposed exterior to distal end 14 of introducer 12, to end 34 where it is pivotably fastened to rivet 36 which is inserted into a hole 35 formed in the head member 21. Hole 35 is located in a generally rectangular shaped recessed area 37 formed on an upper surface and proximate a periphery of head member 21 providing clearance for wire 30 from distal end 20 during rotation. Hole 35 is offset 45° from a lateral axis of head member 21, as will be described shortly, when bipolar electrodes 25 and 26 are longitudinally aligned with introducer 12. This allows the surgeon to provide a moment to head member 21 for easy and selectable rotation of ceramic head member 21 up to 90° about pivot pin 22.

First and second conductors 40 and 42, connect individually to separate electrodes 25 and 26, respectively, projecting from ceramic head member 21. Each conductor 40 and 42 longitudinally extends within lumen 19 to a plug member 50 exterior to proximal end 14. Plug member 50 is connectable to a foot control of an external power generator for selectively energizing bipolar electrodes 25 and 26 during surgery, however, a handle switch could also be used and limitation to a foot control is not to be inferred.

Referring to FIG. 2A, a sectional view of instrument 10 shown in FIG. 1 illustrates first electrode 25 and second electrode 26 (hidden) each having a pair of generally parallel legs 27 and 28, which connect to conductors 40 and 42, respectively, at points 44 and 46. Each wire 40 and 42 longitudinally extends through lumen 19 from exterior plug member 50 to leg portions 27 and 28, respectively, and are routed through wall 49, which terminates lumen 19, of distal end 20 and secured, such as by epoxy, to stress relieve wires 40 and 42 during rotation.

Pull-wire 30 is longitudinally received within tubular opening 48 formed in a wall of working element 18 where opening 48 is sufficiently small in diameter such that wire 30 is slidable within yet avoids kinking. Ceramic head member 21 has a semicircular shaped proximal end closely arranged near wall 49 of the notch formed in yoke-like distal end 20 of working element 18. This arrangement avoids pinching of debris between ceramic head member 21 and wall 49 during rotation. A distal end of head member 21 is rectangular having slightly rounded and smooth edges.

To provide added rigidity, and thus, electrical isolation between bipolar electrodes 25 and 26, once bipolar electrodes 25 and 26 are inserted into ceramic head member 21 in a known manner, a bead of epoxy 67 can be placed at the interface of each electrode 25 and 26 with ceramic head member 21. In the same manner, enhanced stability can be attained by insertion of a stabilizing plug of ceramic or high melting point plastic between electrodes 25 and 26.

Referring to FIG. 2B, in use the surgeon grasps introducer 12 and inserts instrument 10 into the urethral passage with ceramic head member 21 generally longitudinally and coaxially aligned within introducer 12. Next, the surgeon extends head member 21 from introducer 12 by longitudinally sliding working element 18 in the distal direction within introducer 12. Gripping handle loop 33 and selectively retracting loop portion 32 longitudinally outward in the proximal direction provides a moment to pin 36 causing ceramic head member 21 to rotatably pivot about pin 24. Head member 21 is capable of rotation up to 90° in the clockwise direction, as shown, such that electrodes 25 and 26 engage adjacent walls of prostatic tissue. During rotation, hole 35 travels arcuate path "P" where wire 30 is substantially rigid yet pliable enough to bow slightly outward to achieve rotation.

When RF power is supplied from an external power source (not shown) via wires 40 and 42 to closely spaced electrodes 25 and 26, arcing occurs due to a dielectric breakdown between the two loops of electrodes 25 and 26 and proximate tissue is cut and/or cauterized. Electrodes 25 and 26 are substantially identical in size, where neither one assumes the role of a conventional return electrode on a permanent basis. Arcing is found to occur from each electrode to the other. By longitudinally reciprocating loop 32 toward and away from working element 18, ceramic head member 21 reciprocates rotationally to create radial cuts in the prostate gland proximate electrodes 25 and 26 to perform resectioning of the prostate. Because distal end 20 of the instrument is selectively rotatable 360° about a longitudinal axis within introducer 12, this selectable pivoting of ceramic head member 21 allows the surgeon t create radial slices in selected walls of the prostate gland in a convenient fashion.

In summary, the present invention offers the advantage of providing a very effective pivotable bipolar cutting instrument which can be selectively pivoted to create longitudinal incisions in tissue. The invention is also adaptable to other surgical procedures performed using an endoscope and limitations to TURP's is not to be inferred.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. An electrosurgical cutting instrument connectable to a power source comprising:
   (a) a generally tubular working element having a proximal end, a distal end and a lumen extending therebetween;
   (b) a head member comprised of an insulative material pivotally mounted at a pivot point to said distal end of said working element;
   (c) a pair of closely spaced bipolar electrodes extending outward from said head member and separated by a dielectric;
   (d) a pair of conducting wires, insulated from one another and each electrically connected at one end individually to one of said pair of bipolar electrodes, the other ends facilitating connection to said power source; and
   (e) pull-wire means extending through said working element and connected to said head member for pivoting said head member about said pivot point, said wire means being sufficiently rigid such that motioning said wire means towards and away from said proximal end of said working element creates rotation of said head member about said pivot point.

2. The electrosurgical cutting instrument as specified in claim 1, further comprising generally tubular introducer receiving said working element and having a distal end and a proximal end.

3. The electrosurgical cutting instrument as specified in claim 2, wherein said pivot point of said head member is generally coaxially aligned with said introducer and said wire means is pivotably connected to said head member between said pivot point and a periphery of said head member.

4. The electrosurgical cutting instrument as specified in claim 3, wherein said head member is rotatable in at least a 90° angle with respect to said longitudinal axis of said introducer.

5. The electrosurgical cutting instrument as specified in claim 2, wherein said working element is coaxially received and rotatable within said introducer.

6. The electrosurgical cutting instrument as specified in claim 1, wherein said pull-wire means comprises a wire terminating proximate said distal end of said introducer and formed into a loop to form a handle.

7. The electrosurgical cutting instrument as specified in claim 1, wherein said distal end of said working element forms a yoke having a notch receiving said head member.

8. The electrosurgical cutting instrument as specified in claim 7, wherein said head member has an generally semi-circular rounded end located proximate said notch.

9. The electrosurgical cutting instrument as specified in claim 1, wherein each said bipolar electrode has a flattened portion for coagulation.

10. The electrosurgical cutting instrument as specified in claim 1 wherein said bipolar electrodes are spaced from one another a predetermined fixed distance.

11. The electrosurgical cutting instrument as specified in claim 1 wherein said bipolar electrodes are parallel to one another.

12. The electrosurgical cutting instrument as specified in claim 1 wherein each of said bipolar electrodes have a generally U-shape.

13. The electrosurgical cutting instrument as specified in claim 1 wherein at least a portion of each said electrode is disposed within said head member.

* * * * *